United States Patent
Katouzian et al.

(10) Patent No.: US 11,848,100 B2
(45) Date of Patent: Dec. 19, 2023

(54) AUTOMATIC CLINICAL REPORT GENERATION

(71) Applicant: MERATIVE US L.P., Ann Arbor, MI (US)

(72) Inventors: Amin Katouzian, Lexington, MA (US); Anup Pillai, San Jose, CA (US); Marwan Sati, Mississauga (CA)

(73) Assignee: Merative US L.P., Ann Arbor, MI (US)

( * ) Notice: Subject to any disclaimer, the term of this patent is extended or adjusted under 35 U.S.C. 154(b) by 792 days.

(21) Appl. No.: 16/657,506

(22) Filed: Oct. 18, 2019

(65) Prior Publication Data

US 2021/0118536 A1 Apr. 22, 2021

(51) Int. Cl.
| | |
|---|---|
| *G16H 50/20* | (2018.01) |
| *G16H 15/00* | (2018.01) |
| *G16H 30/20* | (2018.01) |
| *G16H 30/40* | (2018.01) |
| *G06N 20/00* | (2019.01) |

(Continued)

(52) U.S. Cl.
CPC ............ *G16H 50/20* (2018.01); *G06F 18/22* (2023.01); *G06N 20/00* (2019.01); *G16H 15/00* (2018.01); *G16H 30/20* (2018.01); *G16H 30/40* (2018.01); *G16H 50/70* (2018.01)

(58) Field of Classification Search
None
See application file for complete search history.

(56) References Cited

U.S. PATENT DOCUMENTS

| | | | |
|---|---|---|---|
| 6,681,060 B2 | 1/2004 | Acharya et al. | |
| 2003/0013951 A1* | 1/2003 | Stefanescu | G06T 7/0012 600/407 |
| 2004/0003001 A1* | 1/2004 | Shimura | G16H 30/20 |

(Continued)

FOREIGN PATENT DOCUMENTS

KR 101604086 B1 3/2016

OTHER PUBLICATIONS

Conjeti et al, Metric Hashing Forests, 2016, Medical Image Analysis, 34, pp. 13-29 (Year: 2016).*

(Continued)

*Primary Examiner* — Gregory Lultschik
(74) *Attorney, Agent, or Firm* — Michael Best & Friedrich LLP

(57) ABSTRACT

Methods and systems for clinical report generation. One system includes an electronic processor configured to receive a query image and determine a similarity metric for a plurality of medical images, where the similarity metric represents a similarity between the query image and each of the plurality of medical images. The electronic processor is also configured to determine a predetermined number of medical images from the plurality of medical images based on the similarity metric for each of the plurality of medical images. The electronic processor is also configured to rank a plurality of reports, where each of the plurality of reports correspond to one of the predetermined number of medical images. The electronic processor is also configured to generate a clinical report including information extracted from at least one of the plurality of reports based on the ranking of the plurality of reports.

15 Claims, 5 Drawing Sheets

(51) Int. Cl.
*G16H 50/70* (2018.01)
*G06F 18/22* (2023.01)

(56) References Cited

U.S. PATENT DOCUMENTS

| | | | | |
|---|---|---|---|---|
| 2007/0237377 | A1* | 10/2007 | Oosawa | G06V 10/25 |
| | | | | 382/128 |
| 2008/0095418 | A1* | 4/2008 | Moriya | A61B 6/563 |
| | | | | 382/128 |
| 2009/0192824 | A1* | 7/2009 | Minakuchi | G16H 15/00 |
| | | | | 705/3 |
| 2010/0189366 | A1* | 7/2010 | Iizuka | G16H 15/00 |
| | | | | 382/209 |
| 2011/0022622 | A1 | 1/2011 | Boroczky et al. | |
| 2011/0166885 | A1* | 7/2011 | Walker | G16H 15/00 |
| | | | | 705/3 |
| 2012/0035963 | A1* | 2/2012 | Qian | G16H 30/20 |
| | | | | 705/3 |
| 2012/0084096 | A1* | 4/2012 | Wang | G16H 15/00 |
| | | | | 705/2 |
| 2015/0317434 | A1* | 11/2015 | Kondo | A61B 5/00 |
| | | | | 705/3 |
| 2017/0140536 | A1* | 5/2017 | Takata | G06T 7/73 |
| 2020/0019617 | A1* | 1/2020 | Eswaran | G06K 9/627 |
| 2021/0166796 | A1* | 6/2021 | Davies | G06F 40/274 |

OTHER PUBLICATIONS

Sabahi et al, Perceptual Image Hashing Using Random Forest for Content-based Image Retrieval, 2018 16th IEEE International New Circuits and Systems Conference (NEWCAS), 2018, pp. 348-351 (Year: 2018).*

Qiu et al Random Forests Can Hash, 2015, arXiv, pp. 1-5 <https://arxiv.org/abs/1412.5083> (Year: 2015).*

Anonymous, "Central Repository for Medical Images and Corresponding Reports", An IP.com Prior Art Database Technical Disclosure, May 8, 2003, ip.com, 5 pages.

Anonymous, "Central Repository for Medical Images and Corresponding Reports", An IP.com Prior Art Database Technical Disclosure, Mar. 25, 2003, ip.com, 6 pages.

* cited by examiner

AUTOMATIC CLINICAL REPORT GENERATION

FIELD

Embodiments described herein relate to automatic clinical report generation, and, more particularly, to automatic clinical report generation through hashing and retrieval.

SUMMARY

Automatically generating a clinical report (for example, a medical imaging report) is a challenge. Existing techniques rely on learning image and text features jointly (often in a manifold space). Learning image and text features jointly generally requires comprehensive training datasets that include both annotated reports and annotated images. Obtaining such comprehensive training datasets are tedious and expensive. Additionally, due to inter- and intra-observation variability in preparing a report, it is very difficult to generate a report automatically such that all observations and interpretations are addressed.

To address these and other problems, embodiments described herein provide automatic clinical report generation. In particular, embodiments described herein provide automatic clinical report generation through retrieving similar medical images and associated reports and automatically ranking and selecting associated reports using image driven clues (image features). In other words, the methods and systems are configured to generate a clinical report for a query image by identifying a predetermined number of medical images similar to the query image and extracting information from one or more reports associated with the identified predetermined number of medical images. Using the information extracted from the similar medical images, the methods and systems described herein generate a clinical report for a user (for example, a reporting radiologist or reporting physician).

Implementations of the methods and systems described herein provide automatic clinical report generation that avoids the need for annotated reports as training data. In other words, the methods and systems described herein provide automatic clinical report generation that may rely solely on image driven clues or features (a set of image features). Additionally, the methods and systems described herein may provide evidence by providing similar images and corresponding reports through retrieval when automatically generating a clinical report. Furthermore, the methods and systems described herein may access (or retrieve) complete reports associated with similar medical images. Since complete reports are accessed (or accessible) the methods and systems described herein may leverage (or provide) complementary or additional information (for example, complimentary information with regard to one or more labels of interest for a medical image).

Accordingly, embodiments described herein provide systems and methods for clinical report generation. For example, one embodiment provides a system for clinical report generation. The system includes an electronic processor configured to receive a query image and determine a similarity metric for a plurality of medical images, where the similarity metric represents a similarity between the query image and each of the plurality of medical images. The electronic processor is also configured to determine a predetermined number of medical images from the plurality of medical images based on the similarity metric for each of the plurality of medical images. The electronic processor is also configured to rank a plurality of reports, where each of the plurality of reports correspond to one of the predetermined number of medical images. The electronic processor is also configured to generate a clinical report including information extracted from at least one of the plurality of reports based on the ranking of the plurality of reports.

Another embodiment provides a method of clinical report generation. The method includes receiving, with an electronic processor, a query image. The method also includes determining, with the electronic processor, a similarity metric for a plurality of medical images, where the similarity metric represents a similarity between the query image and each of the plurality of medical images. The method also includes determining, with the electronic processor, a predetermined number of medical images from the plurality of medical images based on the similarity metric for each of the plurality of medical images. The method also includes ranking, with the electronic processor, a plurality of reports, where each of the plurality of reports correspond to one of the predetermined number of medical images. The method also includes generating, with the electronic processor, a clinical report including information extracted from at least one of the plurality of reports based on the ranking of the plurality of reports.

Yet another embodiment provides a non-transitory computer readable medium including instructions that, when executed by an electronic processor, causes the electronic processor to execute a set of functions. The set of functions includes receiving a query image and determining a similarity metric for a plurality of medical images, where the similarity metric represents a similarity between the query image and each of the plurality of medical images. The set of functions also includes determining a predetermined number of medical images from the plurality of medical images based on the similarity metric for each of the plurality of medical images. The set of functions also includes ranking a plurality of reports, where each of the plurality of reports correspond to one of the predetermined number of medical images. The set of functions also includes generating a clinical report including information extracted from at least one of the plurality of reports based on the ranking of the plurality of reports.

Other aspects of the embodiments will become apparent by consideration of the detailed description and accompanying drawings.

DETAILED DESCRIPTION

Figure 1:
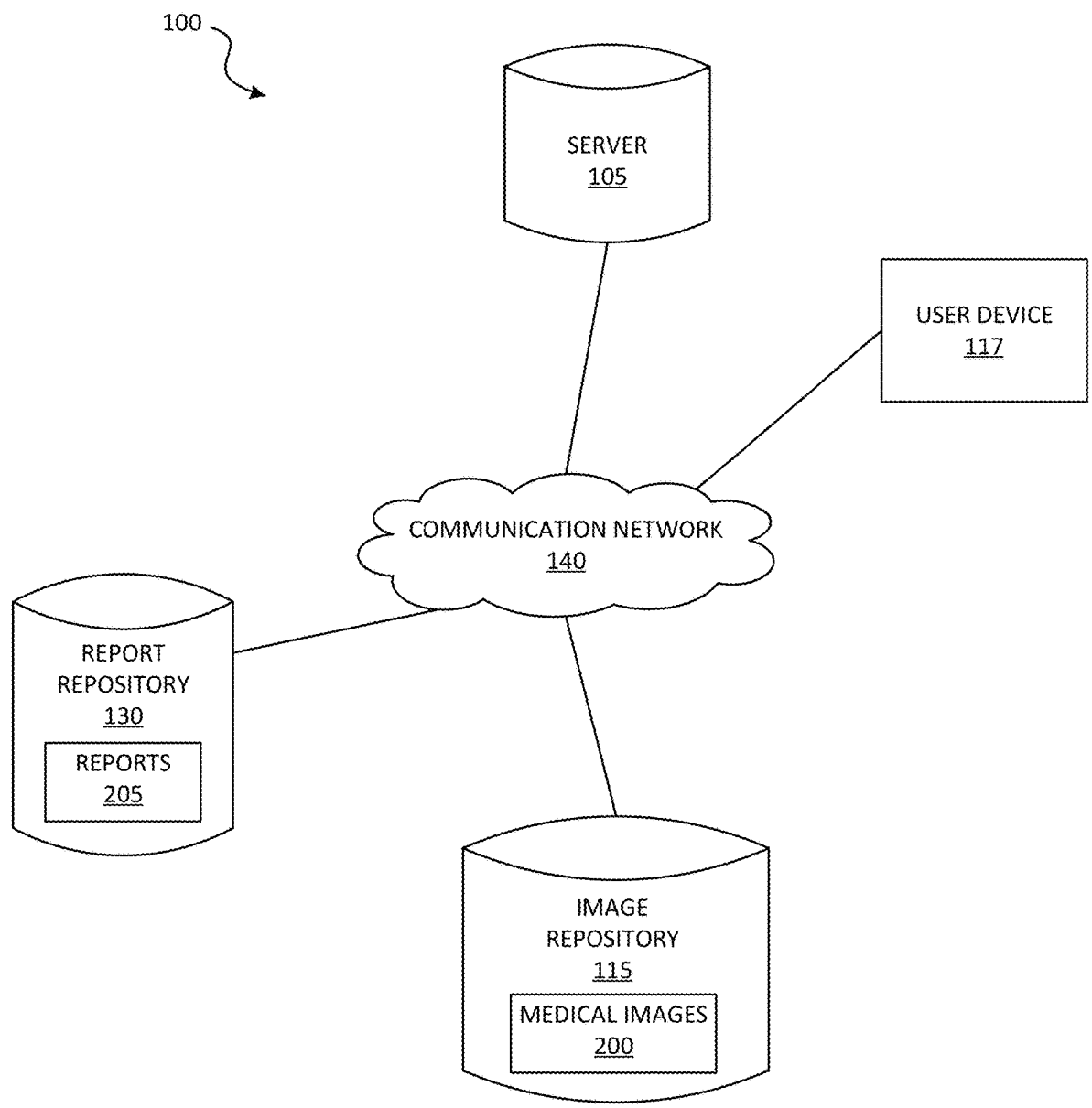
FIG. 1 illustrates a system for clinical report generation according to some embodiments.

One or more embodiments are described and illustrated in the following description and accompanying drawings. These embodiments are not limited to the specific details provided herein and may be modified in various ways.

Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

As described above, automatically generating a clinical report (for example, a medical imaging report) is a challenge. Existing techniques rely on learning image and text features jointly (often in a manifold space). Learning image and text features jointly generally requires comprehensive training datasets that include both annotated reports and annotated images. Obtaining such comprehensive training datasets are tedious and expensive. Additionally, due to inter- and intra-observation variability in preparing a report, it is very difficult to generate a report automatically such that all observations and interpretations are addressed.

To address these and other problems, embodiments described herein provide automatic clinical report generation. In particular, embodiments described herein provide automatic clinical report generation through retrieving similar medical images and associated reports and automatically ranking and selecting associated reports using image driven clues (image features). In other words, the methods and systems are configured to generate a clinical report for a query image by identifying a predetermined number of medical images similar to the query image and extracting information from one or more reports associated with the identified predetermined number of medical images. Using the information extracted from the similar medical images, the methods and systems described herein generates a clinical report for a user (for example, a reporting radiologist or reporting physician).

FIG. 1 schematically illustrates a system 100 for clinical report generation according to some embodiments. The system 100 includes a server 105, an image repository 115, a user device 117, and a report repository 130. In some embodiments, the system 100 includes fewer, additional, or different components than illustrated in FIG. 1. For example, the system 100 may include multiple servers 105, user devices 117, image repositories 115, report repositories 130, or a combination thereof.

The server 105, the image repository 115, the user device 117, and the report repository 130 communicate over one or more wired or wireless communication networks 140. Portions of the communication network 140 may be implemented using a wide area network, such as the Internet, a local area network, such as a Bluetooth™ network or Wi-Fi, and combinations or derivatives thereof. Alternatively or in addition, in some embodiments, components of the system 100 communicate directly as compared to through the communication network 140. Also, in some embodiments, the components of the system 100 communicate through one or more intermediary devices not illustrated in FIG. 1.

Figure 2:
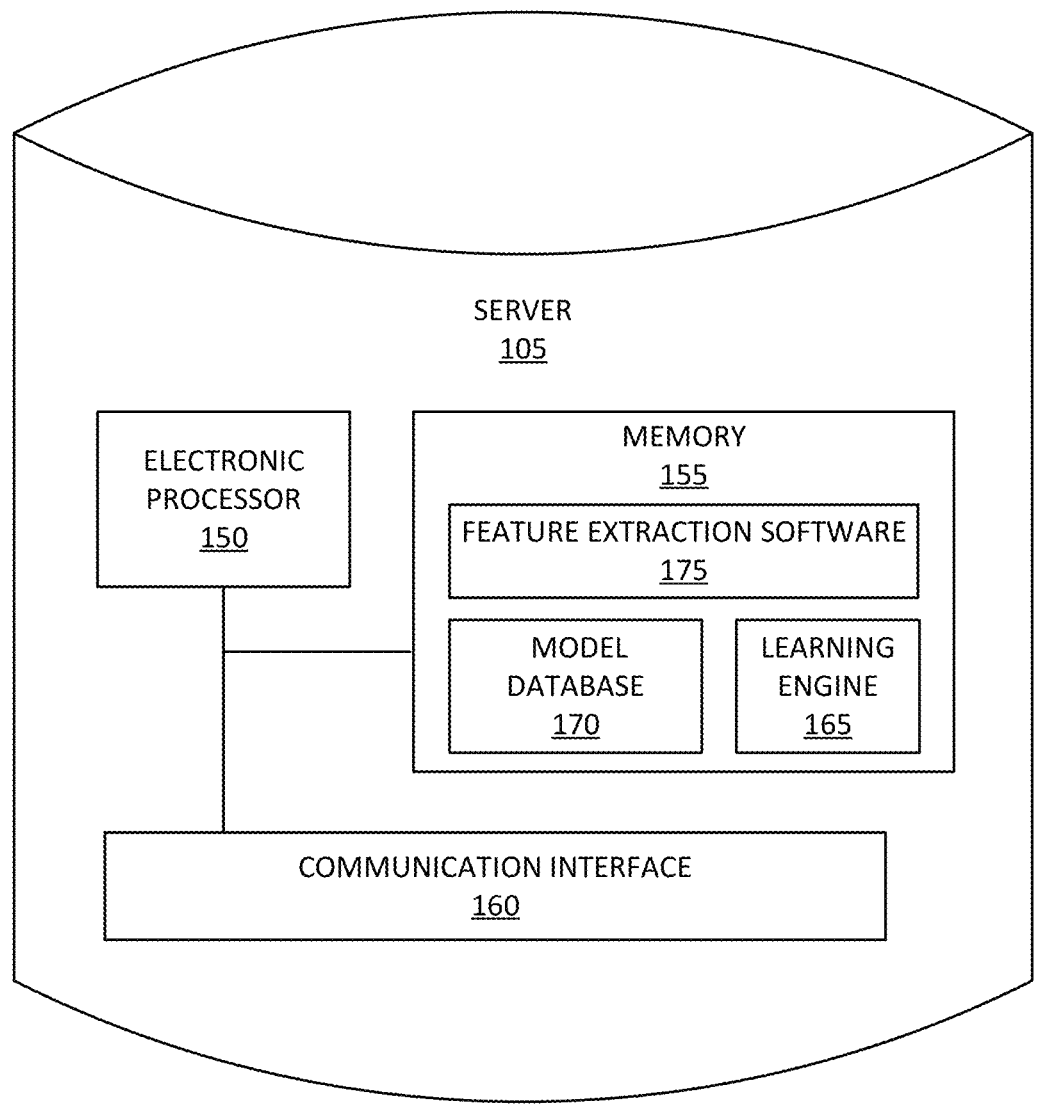
FIG. 2 illustrates a server included in the system of FIG. 1 according to some embodiments.

As illustrated in FIG. 2, the server 105 includes an electronic processor 150, a memory 155, and a communication interface 160. The electronic processor 150, the memory 155, and the communication interface 160 communicate wirelessly, over one or more communication lines or buses, or a combination thereof. The server 105 may include additional components than those illustrated in FIG. 2 in various configurations. The server 105 may also perform additional functionality other than the functionality described herein. Also, the functionality described herein as being performed by the server 105 may be distributed among multiple devices, such as multiple servers included in a cloud service environment. In addition, in some embodiments, the user device 117, the image repository 115, the report repository 130, or a combination thereof may be configured to perform all or a portion of the functionality described herein as being performed by the server 105.

The electronic processor 150 includes a microprocessor, an application-specific integrated circuit (ASIC), or another suitable electronic device for processing data. The memory 155 includes a non-transitory computer readable medium, such as read-only memory ("ROM"), random access memory ("RAM") (for example, dynamic RAM ("DRAM"), synchronous DRAM ("SDRAM"), and the like), electrically erasable programmable read-only memory ("EEPROM"), flash memory, a hard disk, a secure digital ("SD") card, another suitable memory device, or a combination thereof. The electronic processor 150 is configured to access and execute computer-readable instructions ("software") stored in the memory 155. The software may include firmware, one or more applications, program data, filters, rules, one or more program modules, and other executable instructions. For example, the software may include instructions and associated data for performing a set of functions, including the methods described herein.

For example, as illustrated in FIG. 2, the memory 155 may store a learning engine 165 and a model database 170.

In some embodiments, the learning engine 165 develops a model using one or more machine learning functions. Machine learning functions are generally functions that allow a computer application to learn without being explicitly programmed. In particular, a computer application performing machine learning functions (sometimes referred to as a learning engine) is configured to develop an algorithm based on training data or training information. For example, to perform supervised learning, the training data includes example inputs and corresponding desired (for example, actual) outputs, and the learning engine progressively develops a model that maps inputs to the outputs included in the training data. Machine learning may be performed using various types of methods and mechanisms including but not limited to decision tree learning, association rule learning, artificial neural networks, inductive logic programming, support vector machines, clustering, Bayesian networks, reinforcement learning, representation learning, similarity and metric learning, sparse dictionary learning, and genetic algorithms. Using all of these approaches, a computer program may ingest, parse, and understand data and progressively refine models for data analytics, including image analytics.

Accordingly, the learning engine 165 (as executed by the electronic processor 150) may perform machine learning using training data to develop a model that maps a medical image (for example, a query image) to one or more similar medical images. The training data may include, for example, medical images and their associated image features. For example, the learning engine 165 may identify one or more unique characteristics of a medical image (for example, image features associated with the medical image, metadata associated with the medical image, and the like) and develop a model that maps the one or more unique characteristics to one or more similar medical images (for example, one or more unique characteristics or image features associated with the medical images). Accordingly, when a subsequent medical image is received (for example, a query image), the electronic processor 125 may determine one or more medical images similar to that subsequent medical image using the model developed by the learning engine 145.

In some embodiments, the models generated by the learning engine 165 and stored in the model database 170 are hashing models (for example, an ensemble of metric hashing forests). In some instances, each of the hashing models of the ensemble of metric hashing forests is associated with a different length (for example, 32 bit, 64 bit, 128 bit, 256 bit, 512 bit, 1024 bit, and the like). In some embodiments, the learning engine 165 (for example, the electronic processor 150) develops the hashing model with machine learning using a plurality of medical images and an associated set of image features for each of the medical images (training information or data). In other words, the hashing model may be trained on image level data (for example, image features, such as image level labels), where the trained hashing model then encodes each data in the training information.

Models generated by the learning engine 165 may be stored in the model database 170. As illustrated in FIG. 2, the model database 170 is included in the memory 155 of the server 105. It should be understood that, in some embodiments, the model database 170 is included in a separate device accessible by the server 105 (included in the server 105 or external to the server 105).

As illustrated in FIG. 2, the memory 155 may also store feature extraction software 175. The feature extraction software 175 is, for example, object recognition or detection software. For example, the feature extraction software 175 may be a deep convolution network for object recognition, such as a Visual Geometry Group (VGG) FC7 network. Accordingly, the feature extraction software 175 extracts one or more image features from a medical image. For example, in some embodiments, the electronic processor 150 uses the feature extraction software 175 to analyze a medical image and extract one or more image features (a set of image features) from the medical image. An image feature extracted from the medical image may be stored in the memory 155 or another remote storage location. In some embodiments, the feature extraction software 175 is a medical diagnostic software with object recognition functionality. The type of medical diagnostic software the feature extraction software 175 is may be dependent on a type of medical image in which image features are extracted.

The communication interface 160 allows the server 105 to communicate with devices external to the server 105. For example, as illustrated in FIG. 1, the server 105 may communicate with the image repository 115, the user device 117, the report repository 130, or a combination thereof through the communication interface 160. In particular, the communication interface 160 may include a port for receiving a wired connection to an external device (for example, a universal serial bus ("USB") cable and the like), a transceiver for establishing a wireless connection to an external device (for example, over one or more communication networks 140, such as the Internet, local area network ("LAN"), a wide area network ("WAN"), and the like), or a combination thereof.

As illustrated in FIG. 1, the image repository 115 stores a plurality of medical images 200 (referred to herein collectively as "the medical images 200" and individually as "a medical image 200"). A medical image may include, for example, a chest x-ray, an MIll, a CT scan, and the like. The medical images 200 are images captured by a medical imaging device (not shown), such as an MM, CT, and the like. For example, a medical image 200 may be a chest x-ray or an MRI image. In some embodiments, the medical images 200 are captured by a medical imaging device and transmitted (via the communication network 140) to the image repository 115 for storage.

Accordingly, the image repository 115 provides for the storage and retrieval of the medical images 200. In some embodiments, the medical images 200 may be stored within a plurality of databases, such as within a cloud service. Although not illustrated in FIG. 1, the image repository 115 may include components similar to the server 105, such as an electronic processor, a memory, a communication interface and the like. For example, the image repository 115 may include a communication interface configured to communicate (for example, receive data and transmit data) over the communication network 140. In some embodiments, the medical images 200 stored in the image repository 115 are used as the training information for the models stored in the model database 170.

The report repository 130 stores a plurality of reports 205 (referred to herein collectively as "the reports 205" and individually as "a report 205"). In some embodiments, each of the reports 205 stored in the report repository 130 correspond with one or more of the medical images 200 of the image repository 115. In other words, a report 205 includes information associated with at least one corresponding medical image 200, such as patient identification information, a diagnosis, a comment or note regarding the associated medical image, a medical finding, and the like. In some embodiments, the information includes a label (or a class) associated with the corresponding medical image 200.

A label may define a disease or condition detected or not detected in a corresponding medical image 200, such as, for example, atelectasis, opacity, edema, pleural thickening, emphysema, mass/nodule, pneumothorax, fibrosis, and the like. Accordingly, the image repository 115 provides for the storage and retrieval of the reports 205 corresponding to the medical images 200 stored in the image repository 115. In some embodiments, the image repository 115 and the report repository 130 are combined to form a single repository that stores the reports 205 and the corresponding medical images 200. Alternatively or in addition, the reports 205 may be stored within a plurality of databases, such as within a cloud service. Although not illustrated in FIG. 1, the report repository 130 may include components similar to the server 105, such as an electronic processor, a memory, a communication interface and the like. For example, the report repository 130 may include a communication interface configured to communicate (for example, receive data and transmit data) over the communication network 140.

The user device 117 is a computing device and may include a desktop computer, a terminal, a workstation, a laptop computer, a tablet computer, a smart watch or other wearable, a smart television or whiteboard, or the like. Although not illustrated, the user device 117 may include similar components as the server 105 (an electronic processor, a memory, and a communication interface). The user device 117 may also include a human-machine interface for interacting with a user. The human-machine interface may include one or more input devices, one or more output devices, or a combination thereof. Accordingly, in some embodiments, the human-machine interface allows a user to interact with (for example, provide input to and receive output from) the user device 117. For example, the human-machine interface may include a keyboard, a cursor-control device (for example, a mouse), a touch screen, a scroll ball, a mechanical button, a display device (for example, a liquid crystal display ("LCD")), a printer, a speaker, a microphone, or a combination thereof. In some embodiments, the human-machine interface includes a display device. The display device may be included in the same housing as the user device 117 or may communicate with the user device 117 over one or more wired or wireless connections. For example, in some embodiments, the display device is a touchscreen included in a laptop computer or a tablet computer. In other embodiments, the display device is a monitor, a television, or a projector coupled to a terminal, desktop computer, or the like via one or more cables. Some of these devices may have severe memory or computational capacity constraints placing an even greater emphasis on intelligent prefetching of a study or a study element.

A user may use the user device 117 to access and view the medical images 200. Additionally, a user may use the user device 117 to prepare reports (for example, the reports 205 or a new clinical report) corresponding to the medical images 200 or a new medical image. Accordingly, in some embodiments, the user device 117 is a workstation for interpreting, reviewing, and reporting on medical images. For example, a radiologist may use the user device 117 as a workstation to review a patient's medical image (a query image) and prepare or generate a report (a clinical report) associated with that patient's medical image. In some embodiments, a secured network is used for the transmission of patient information between the components of the system 100 (for example, the communication network 140). In some embodiments, the functionality (or a portion thereof) described as being performed by the user device 117 is performed by the server 105.

As noted above, automatically generating a clinical report (for example, a medical imaging report) is a challenge because, among other things, it requires a particular training dataset. Accordingly, to solve this and other problems, the system 100 is configured to generate a clinical report for a query image by identifying a predetermined number of medical images similar to the query image and extracting information from one or more reports associated with the predetermined number of medical images. Using the information extracted from the similar medical images, the methods and systems described herein generates a clinical report for a user (for example, a reporting radiologist or reporting physician).

Figure 3:
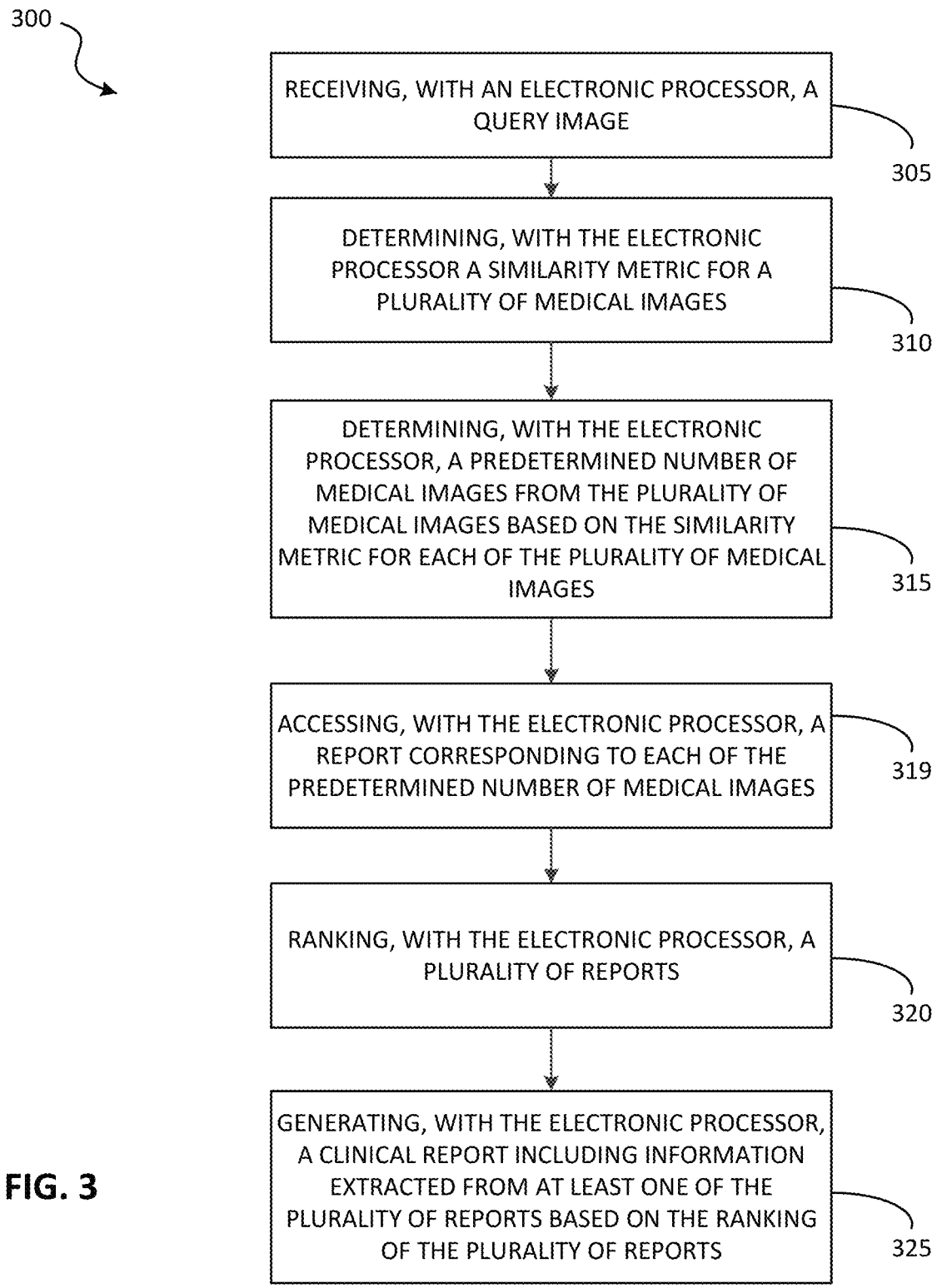
FIG. 3 is a flowchart illustrating a method for clinical report generation using the system of FIG. 1 according to some embodiments.
Figure 4:
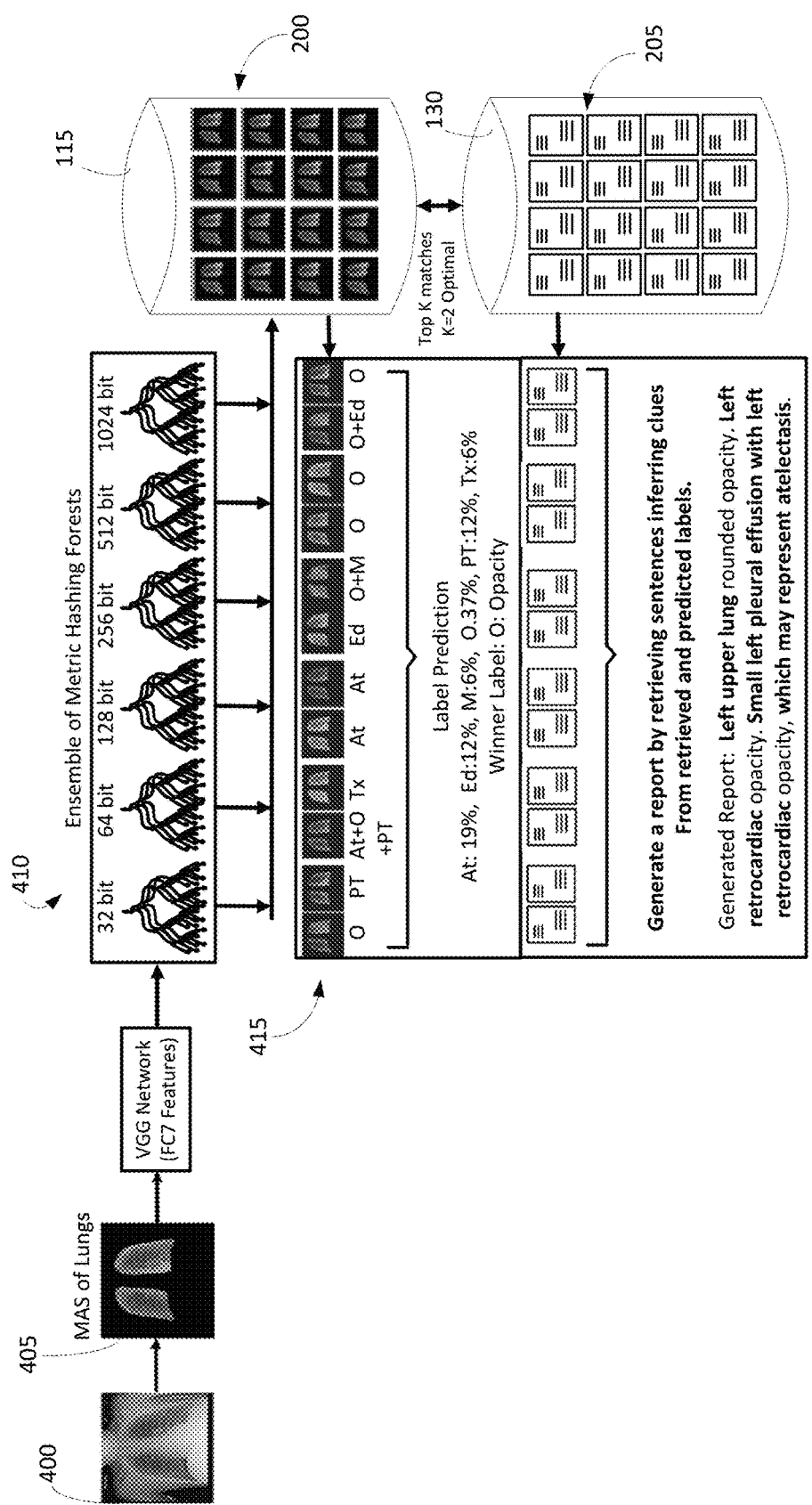
FIG. 4 is a block diagram illustrating an overview of the method of FIG. 3 according to some embodiments.

For example, FIG. 3 is a flowchart illustrating a method 300 for clinical report generation according to some embodiments. FIG. 4 is a block diagram illustrating an overview of the method 300. The method 300 is described herein as being performed by the server 105 (the electronic processor 150 executing instructions). However, as noted above, the functionality performed by the server 105 (or a portion thereof) may be performed by other devices, including, for example, the user device 117 (via an electronic processor executing instructions).

In some embodiments, the method 300 is initiated in response to a user action performed at the user device 117. In some instances, the method 300 is automatically initiated when a user accesses a medical image (i.e., the query image) and initiates a reporting process for the medical image (for example, by opening a reporting user interface or window, by opening a reporting application, or the like) or other triggering events, such as the generation or storage of the query image. However, in other instances, the method 300 is manually initiated in response to a user requesting initiation of the method 300 (for example, by selecting a button or other type of mechanism within a reporting application).

As illustrated in FIG. 3, the method 300 includes receiving, with the electronic processor 150, a query image 400 (at block 305). The query image 400 is, for example, a medical image associated with a patient. In some embodiments, the query image 400 is a medical image (recently) captured by a medical imaging device that does not yet have an associated clinical report. In other embodiments, the query image 400 may already be associated with a clinical report (a partial or complete report). For example, the automatic report generation disclosed herein may be used as a check or second opinion for other automatically or manually generated report.

In some embodiments, the electronic processor 150 receives the query image 400 directly from a medical imaging device through the communication network 140. For example, when a new medical image is ordered for a patient and captured by a medical imaging device, the new medical image is transmitted from the medical imaging device to the electronic processor 150 such that a clinical report may be generated (or prepared) for the new medical image. Alternatively or in addition, in some embodiments, the electronic processor 150 receives the query image 400 from a storage device (for example, a memory of the user device 117, the image repository 115, or another storage device) in response to a request for the query image 400 by a user. For example, a user may use the user device 117 to initiate a request for a particular medical image (i.e., the query image 400) associated with a patient to prepare a report associated with that particular medical image. In response to receiving the request, the electronic processor 150 receives (accesses) the query image 400 from a storage location, such as a memory of the user device 117 or the image repository 115. Accordingly, in some embodiments, the query image 400 received by the electronic processor 150 is a previously-stored medical image and is included in the medical images 200 stored in the image repository 115.

The electronic processor 150 analyzes the query image 400. In some embodiments, the electronic processor 150 analyzes the query image 400 to perform pre-processing, such as to perform image segmentation (MAS of lungs 405 illustrated in FIG. 4), a histogram equalization, another type of pre-processing, or a combination thereof. The electronic processor 150 also analyzes the query image 400 using the feature extraction software 175 to extract one or more features (for example, image features) associated with the query image 400. The extracted features are used with (input to) a model 410, such as a hashing model stored in the model database 170. For example, the electronic processor 150 may analyze the query image 400 (the extracted features) with a hashing model to determine one or more hash values associated with the query image 400. The hash values associated with the query image 400 can be stored, for example, in the memory 155.

Figure 5:
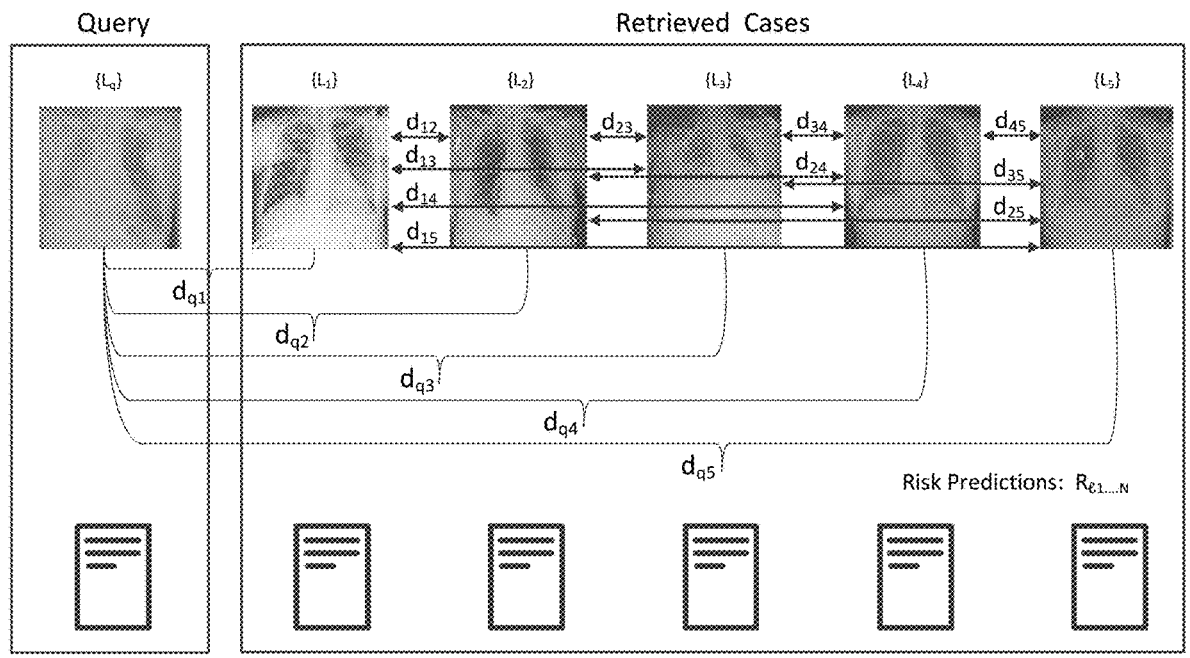
FIG. 5 illustrates various hamming distances between a query image and a plurality of similar medical images according to some embodiments.

Using the hash values for the query image 400, the electronic processor 150 determines a similarity metric for a plurality of medical images (for example, the medical images 200) (at block 310). The similarity metric represents a similarity between the query image 400 and each of the medical images 200 stored in the image repository 115. In some embodiments, the electronic processor 150 determines the similarity metric for each of the medical images 200 by determining hash values, for example, using the ensemble of metric hashing forests described above, and comparing the hash values to the hash values for the query image 400. Accordingly, the similarity metric may be a hamming distance. For example, FIG. 5 illustrates various hamming distances. In some embodiments, the hamming distance represents a similarity between the query image 400 and each of the medical images 200. Alternatively or in addition, in some embodiments, the hamming distance represents a similarity between each of the medical images 200. A hamming distance may represent a distance (or similarity) between the query image 400 and each of the medical images 200 such that a lower hamming distance represents a closer (or higher) similarity between the query image 400 and a medical image 200 while a higher hamming distance represents a farther (or lower) similarity between the query image 400 and a medical image 200.

In some embodiments, rather than using the hashing model, the electronic processor 150 determines the similarity metric by extracting image features from the query image, one or more medical images 200, or a combination thereof with the feature extraction software 175 (for example, with a deep convolution network for object recognition). The electronic processor 150 may determine a similarity between the query image and one or more of the medical images 200 based on a comparison of extracted image features. For example, the electronic processor 150 may extract a first set of image features from the query image and extract a second set of image features from each of the medical images 200. The electronic processor 150 may compare the first set of image features and the second set of image features. Based on the comparison, the electronic processor 150 may determine a similarity metric for each of the medical images (200) (how similar each of the medical images 200 is to the query image).

After determining the similarity metric for each of the medical images 200, the electronic processor 150 determines a predetermined number of medical images 415 from the medical images 200 based on the similarity metric for each of the medical images 200 (at block 315). The predetermined number of medical images 415 includes a set of medical images having the most similarity with the query image 400. In other words, the electronic processor 150 determines or identifies which of the medical images 200 are the best matches or the closest matches to the query image 400. As noted above, the similarity metric represents a similarity between the query image 400 and each of the medical images 200. Accordingly, the electronic processor 150 may determine the predetermined number of medical images 415 by comparing the similarity metric for each of the medical images 200. In other words, the electronic processor 150 may rank or sort each of the medical images 200 based on their corresponding similarity metric. After ranking or sorting each of the medical images 200 based on their corresponding similarity metric, the electronic processor 150 may determine the predetermined number of medical images 415 as the highest ranking (or highest positioned in a sorted listing of the medical images 200). In some embodiments, the predetermined number of medical images 415 is a preset number of medical images. For example, in such embodiments, the electronic processor 150 determines the predetermined number of medical images 415 from the medical images 200 to include the top two most similar medical images (the two closest matches) to the query image 400.

As noted above, each of the medical images 200 have a corresponding report (for example, the reports 205 of the report repository 130). The electronic processor 150 may access the corresponding reports 205 for each of the medical images 200 included in the predetermined number of medical images 415 (at block 319). After accessing the corresponding reports 205 from the report repository 130 (via the communication network 140), the electronic processor 150 ranks the reports 205 (at block 320). In some embodiments, the electronic processor 150 ranks the corresponding reports 205 based on image driven data or features (for example, a set of image features) from the corresponding images (the predetermined number of medical image 415). Image driven data or features may include, for example, a label associated with a medical image, a similarity metric (i.e., a hamming distance) between the medical image and the query image 400 or other images in the predetermined number of medical images 415, a risk prediction associated with a label associated with the medical image 200, another image driven feature, or a combination thereof. In some embodiments, the image driven data or features may be taken into account as part of weighting a report 205, which may then be used to determine a ranking. For example, common features among the predetermined number of medical images 415 may represent "likely" features associated with the report for the query image 400. Accordingly, the reports 205 associated with these images 415 (the images 415 in the "majority") may be weighted higher than reports 205 associated with other images 415 (the images 415 not in the "majority"). For example, if a majority (or another percentage satisfying a predetermined threshold) of the predetermined number of images 415 are associated with the label "opacity," this may represent the "wining" or "likely" label and the reports 205 associated with these images 415 may be ranked higher than reports associated with other images 415. Similar weighting may be used for reports 205 associated with images 415 that have a shorter hamming distance to the query image 400 than other images 415.

As illustrated in FIG. 3, the electronic processor 150 automatically generates a clinical report using the identified similar images 415 and the corresponding reports 205 (as weighted or ranked) (at block 325). The clinical report may include information extracted from at least one of the corresponding reports 205 for the images 415. In some embodiments, the electronic processor 150 extracts the information based on the ranking of the reports 205. In some embodiments, the electronic processor 150 generates the clinical report using information extracted from more than one of the corresponding reports 205. For example, the electronic processor 150 may extract a first portion of information from a first report and a second portion of information from a second report. The electronic processor 150 may generate the clinical report such that the clinical report includes the first portion of information from the first report and the second portion of information from the second report. In some embodiments, the electronic processor 150 determines a ranking associated with each portion of information included in each of the corresponding reports 250. In such embodiments, the electronic processor determines which portion of information to extract from the corresponding reports 205 based on the ranking associated with each portion of information. For example, the electronic processor 150 may perform an optimization process to identify or determine which of the corresponding reports 205 includes the best or most complete information for a particular portion of information. In some embodiments, the electronic processor 150 generates the clinical report by aggregating (or combining) information from more than one of the corresponding reports 205.

In some embodiments, as part of generating the clinical report, the electronic processor 150 predicts a label for the query image based on one or more labels associated with each of the predetermined number of medical images. For example, where a majority of the corresponding reports 205 indicate (or include) a particular label, the electronic processor 150 may predict that the clinical report for the query image should also indicate (or include) that particular label. When the electronic processor 150 predicts a label for the query image, the electronic processor 150 may generate the clinical report such that the clinical report includes the predicted label for the query image.

In some instances, a medical imaging report (for example, the clinical report) may need to follow a specific format or template, such as ACR BI-RADS, PI-RADS, LI-RADS, and the like. Accordingly, in some embodiments, the electronic processor 150 performs a normalization process to generate a normalized version of the generated clinical report. In such embodiments, the electronic processor 150 may review and extract, from the reports 205, information necessary for the normalized version of the generated clinical report. The electronic processor 150 may establish a correlation among the extracted information, image findings, reports findings, or a combination thereof. The electronic processor 150 may further perform an optimization to identify or determine best matches. After identifying the best matches, the electronic processor 150 may populate a normalized version of the generated clinical report with the best matches. In some embodiments, the normalized version of the generated clinical report includes all required fields are filled and is provided in a free text form. Accordingly, in some embodiments, the electronic processor 150 normalizes the reports 205 by extracting information from each of the reports 205 and generating a new version for each of the reports 205 such that the new version for each of the reports 205 follow the same template.

In some embodiments, the electronic processor 150 generates the clinical report for display to a user via the user device 117. Accordingly, in such embodiments, the electronic processor 150 generates and transmits the clinical report to the user device 117 (via the communication network 140) for display using a display device of the user device 117. The user may then interact with the generated clinical report. For example, a user may edit the information included in the clinical report, add additional information to the clinical report, remove information from the clinical report, access complementary or additional information associated with the automatically generated clinical report, view supporting evidence used for automatically generating the clinical report, and the like via, for example, the user device 117.

Accordingly, embodiments described herein provide automatic clinical report generation. In particular, the embodiments described herein provide automatic clinical report generation through retrieving similar medical images and associated report and automatically ranking and selecting associated reports using image driven clues (image features). In other words, the methods and systems are configured to generate a clinical report for a query image by identifying a predetermined number of medical images similar to the query image and extracting information from one or more reports associated with the predetermined number of medical images. Using the information extracted from similar medical images, the methods and systems described herein generates a clinical report for a user (for example, a reporting radiologist or reporting physician). Accordingly, machine learning is used with respect to the images only (as compared to both the images and associated reports), which decreases the complexities and requirements for performing the machine learn. After similar images are identified, the associated reports are retrieved and information from the reports is leveraged based on the similar images and the query image. For example, the reports can be weighted using clues driving from the images (such as degree of similarity between associated image and query image, "wining" label, and the like), and relevant information can be extracted from the weighted reports for inclusion in the automatically-generated clinical report.

Implementations of the methods and systems described herein provide automatic clinical report generation that avoids the need for annotated reports as training data. In other words, the methods and systems described herein provide automatic clinical report generation that may rely solely on image driven clues or features (a set of image features). Additionally, the methods and systems described herein may provide evidence when automatically generating a clinical report. Furthermore, the methods and systems described herein may access (or retrieve) complete reports associated with similar medical images. Since complete reports are accessed (or accessible) the methods and systems described herein may leverage (or provide) complementary or additional information (for example, complimentary information with regard to one or more labels of interest for a medical image).

The tables below provide a performance overview of the methods and systems described herein. In particular, the methods and systems described herein were trained using a dataset of 32272 medical images from the National Institute of Health (NIH), where the dataset excluded medical images associated with hernia, cardiomegaly, or no finding labels. The methods and systems described herein were then implemented on a test set of 15373 medical images. Table 1 (below) outlines reported hits using an accumulative model consensus. Table 2 (below) outlines reported statistics per class (or label).

TABLE 1

| Encoding | One Hit | Two Hits | Three Hits | Four Hits | Five Hits | Total Hits | | Perfect Hit | |
|---|---|---|---|---|---|---|---|---|---|
| 32 | 6813 | 1620 | 229 | 45 | 6 | 8713 | 56.68% | 3841 | 25.00% |
| 64 | 7846 | 2831 | 619 | 126 | 13 | 11435 | 74.38% | 6637 | 43.17% |
| 128 | 8090 | 3408 | 943 | 178 | 31 | 12650 | 82.29% | 8449 | 54.96% |
| 256 | 8161 | 3785 | 1122 | 237 | 44 | 13349 | 86.83% | 9707 | 63.14% |
| 512 | 8199 | 3986 | 1248 | 288 | 45 | 13766 | 89.55% | 10550 | 68.63% |
| 1024 | 8154 | 4140 | 1331 | 320 | 55 | 14000 | 91.07% | 11112 | 72.28% |

TABLE 2

| Class | Specificity (%) | Sensitivity (%) | Accuracy (%) | Precision (%) |
|---|---|---|---|---|
| Atelectasis | 74.10 | 31.59 | 68.65 | 15.20 |
| Opacity | 33.44 | 68.61 | 43.98 | 30.61 |
| Edema | 94.30 | 11.35 | 91.29 | 6.94 |
| Pleural Thickening | 64.29 | 42.76 | 59.67 | 24.65 |
| Emphysema | 95.83 | 59.95 | 91.99 | 5.98 |
| Mass/Nodule | 72.12 | 32.63 | 67.41 | 13.68 |
| Pneumothorax | 91.30 | 12.46 | 83.10 | 14.27 |
| Fibrosis | 97.20 | 6.21 | 95.65 | 3.69 |

It should be understood that although embodiments described herein used images of lungs and reports providing findings for various lung diseases, the embodiments described here in applicable to any type of imaging, any part of anatomy, and any type of disease or condition where a report is generated for one or more images. Also, it should be understood that the embodiments described herein can be used with two-dimensional or three-dimensional images.

Various features and advantages of the invention are set forth in the following claims.

What is claimed is:

1. A system for clinical report generation, the system comprising:
   an electronic processor configured to
      develop a plurality of hashing models with machine learning using training data, the training data including image level data, each of the plurality of hashing models associated with a different bit length,
      receive a query image,
      determine a similarity metric for each of a plurality of medical images, wherein the similarity metric represents a similarity between the query image and each of the plurality of medical images, wherein the similarity metric for each of the plurality of medical images is determined using the plurality of hashing models,
      determine a predetermined number of medical images from the plurality of medical images based on the similarity metric for each of the plurality of medical images,
      rank a plurality of reports based on a label included in each of the plurality of reports, wherein each of the plurality of reports correspond to one of the predetermined number of medical images,
      generate a clinical report, including information extracted from at least one of the plurality of reports, based on the ranking of the plurality of reports, and
   provide the generated clinical report for user interaction,
      wherein ranking the plurality of reports based on the label included in each of the plurality of reports includes ranking a first report of the plurality of reports higher than a second report of the plurality of reports in response to the label included in the first report being associated with a percentage of the plurality of medical images satisfying a predetermined threshold.

2. The system of claim 1, wherein the training information includes the plurality of medical images and an associated set of image features for each of the plurality of medical images.

3. The system of claim 1, wherein the similarity metric is a hamming distance.

4. The system of claim 1, wherein the electronic processor is configured to determine the similarity metric by
   extracting a first set of image features from the query image,
   extracting a second set of image features from each of the plurality of medical images, and
   determining the similarity metric for each of the plurality of medical images based on a comparison of the first set of image features and the second set of image features.

5. The system of claim 4, wherein the electronic processor is configured to extract the first set of image features and the second set of image features using a deep convolution network for object recognition.

6. The system of claim 1, wherein the electronic processor is further configured to predict a label for the query image based on labels associated with each of the predetermined number of medical images, wherein the clinical report includes the predicted label for the query image.

7. The system of claim 1, wherein the predetermined number of medical images includes a set of medical images having the most similarity with the query image.

8. A method for clinical report generation, the method comprising:
   developing, with an electronic processor, a plurality of hashing models with machine learning using training data, the training data including image level data, each of the plurality of hashing models associated with a different bit length,
   receiving, with the electronic processor, a query image,
   determining, with the electronic processor, a similarity metric for each of a plurality of medical images, wherein the similarity metric represents a similarity between the query image and each of the plurality of medical images, wherein the similarity metric for each of the plurality of medical images is determined using the plurality of hashing models,
   determining, with the electronic processor, a predetermined number of medical images from the plurality of medical images based on the similarity metric for each of the plurality of medical images,
   ranking, with the electronic processor, a plurality of reports based on a label included in each of the plurality of reports, wherein each of the plurality of reports correspond to one of the predetermined number of medical images, generating, with the electronic processor, a clinical report, including information extracted from at least one of the plurality of reports, based on the ranking of the plurality of reports, and providing the generated clinical report for user interaction, wherein ranking the plurality of reports based on the label included in each of the plurality of reports includes ranking a first report of the plurality of reports higher than a second report of the plurality of reports in response to the label included in the first report being associated with a percentage of the plurality of medical images satisfying a predetermined threshold.

9. The method of claim 8, further comprising:

predicting a label for the query image based on labels associated with each of the predetermined number of medical images, wherein the clinical report includes the predicted label for the query image.

10. The method of claim 8, further comprising:

normalizing the plurality of reports by extracting information from each of the plurality of reports and generating a new version for each of the plurality of reports such that the new version for each of the plurality of reports follow the same template.

11. The method of claim 8, wherein generating the clinical report includes extracting a first portion of information from a first report included in the plurality of reports, and extracting a second portion of information from a second report included in the plurality of reports, wherein the clinical report includes the first portion of information and the second portion of information.

12. A non-transitory computer readable medium including instructions that, when executed by an electronic processor, causes the electronic processor to execute a set of functions, the set of functions comprising:

developing a plurality of hashing models with machine learning using training data, the training data including image level data, each of the plurality of hashing models associated with a different bit length, receiving a query image, determining a similarity metric for each of a plurality of medical images, wherein the similarity metric represents a similarity between the query image and each of the plurality of medical images, wherein the similarity metric for each of the plurality of medical images is determined using the plurality of hashing models, determining a predetermined number of medical images from the plurality of medical images based on the similarity metric for each of the plurality of medical images;

ranking a plurality of reports based on a label included in each of the plurality of reports, wherein each of the plurality of reports correspond to one of the predetermined number of medical images, generating a clinical report, including information extracted from at least one of the plurality of reports, based on the ranking of the plurality of reports, and providing the generated clinical report for user interaction, wherein ranking the plurality of reports based on the label included in each of the plurality of reports includes ranking a first report of the plurality of reports higher than a second report of the plurality of reports in response to the label included in the first report being associated with a percentage of the plurality of medical images satisfying a predetermined threshold.

13. The computer readable medium of claim 12, wherein the training information includes the plurality of medical images and an associated set of image features for each of the plurality of medical images.

14. The computer readable medium of claim 12, wherein the set of functions further comprises:

predicting a label for the query image based on labels associated with each of the predetermined number of medical images, wherein the clinical report includes the predicted label for the query image.

15. The computer readable medium of claim 12, wherein the set of functions further comprises:

normalizing the plurality of reports by extracting information from each of the plurality of reports and generating a new version for each of the plurality of reports such that the new version for each of the plurality of reports follow the same template.

* * * * *